(12) United States Patent
Zucherman et al.

(10) Patent No.: US 6,652,534 B2
(45) Date of Patent: Nov. 25, 2003

(54) APPARATUS AND METHOD FOR DETERMINING IMPLANT SIZE

(75) Inventors: James F. Zucherman, San Francisco, CA (US); Ken Y. Hsu, San Francisco, CA (US); Charles J. Winslow, Walnut Creek, CA (US); Scott Yerby, Montara, CA (US); John Flynn, Concord, CA (US)

(73) Assignee: St. Francis Medical Technologies, Inc., Concord, CA (US)

( * ) Notice: Subject to any disclaimer, the term of this patent is extended or adjusted under 35 U.S.C. 154(b) by 196 days.

(21) Appl. No.: 09/978,387

(22) Filed: Oct. 16, 2001

(65) Prior Publication Data

US 2002/0111679 A1 Aug. 15, 2002

Related U.S. Application Data

(63) Continuation-in-part of application No. 09/799,470, filed on Mar. 5, 2001, which is a continuation-in-part of application No. 09/473,173, filed on Dec. 28, 1999, now Pat. No. 6,235,030, which is a continuation of application No. 09/179,570, filed on Oct. 27, 1998, now Pat. No. 6,048,342, which is a continuation-in-part of application No. 09/175,645, filed on Oct. 20, 1998, now Pat. No. 6,068,630
(60) Provisional application No. 60/306,099, filed on Jul. 17, 2001.

(51) Int. Cl.$^7$ ............................................... A61B 17/56
(52) U.S. Cl. ........................................ 606/102; 606/61
(58) Field of Search ........................... 606/60, 61, 99, 606/102, 105; 623/17.11, 17.16

(56) References Cited

U.S. PATENT DOCUMENTS

| | | | |
|---|---|---|---|
| 2,677,369 A | 5/1954 | Knowles | |
| 3,426,364 A | 2/1969 | Lumb | |
| 3,648,691 A | 3/1972 | Lumb et al. | |

(List continued on next page.)

FOREIGN PATENT DOCUMENTS

| | | |
|---|---|---|
| CA | 2015507 | 1/1991 |
| DE | 2821678 A1 | 4/1980 |

(List continued on next page.)

OTHER PUBLICATIONS

Minns, R.J., et al., *Preliminary Design and Experimental Studies of a Novel Soft Implant for Correcting Sagittal Plane Instability in the Lumbar Spine*, Spine vol. 22, No. 16, pp. 1819–1825, © 1997, Lippincott–Raven Publishers.

Waldemar Link, brochure entitled *Wirbelsäulen–Chirurgie: Instrumentarium Und Implantate Zur Wirbelsäulen–Chirurgie* (Spinal Surgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77–86, ©1990 Raven Press, Ltd., New York.

Richard W. Porter, MD, FRCS, FRCSE, *Spinal Stenosis and Neurogenic Claudication*, Spine vol. 21, No. 17, pp. 2046–2052, ©1996, Lippincott–Raven Publishers.

*Primary Examiner*—David O. Reip
(74) *Attorney, Agent, or Firm*—Fliesler Dubb Meyer & Lovejoy LLP

(57) ABSTRACT

A method and apparatus for determining the space between adjacent spinous process. A trial implant instrument contains a trial sizer and an elongated body. The trial sizer and elongated body are pivotally mounted so that as the trial sizer is urged between adjacent spinous process, a physician may rotate the elongated body through a range of motion and not place any torsional forces upon the trial sizer. The method comprises several steps whereby a physician inserts and removes trial implant instruments with sizers of varying diameters to determine the space between adjacent spinous process.

61 Claims, 5 Drawing Sheets

U.S. PATENT DOCUMENTS

| | | |
|---|---|---|
| 3,867,728 A | 2/1975 | Stubstad et al. |
| 3,875,595 A | 4/1975 | Froning |
| 4,309,777 A | 1/1982 | Patil |
| 4,347,845 A | 9/1982 | Mayfield |
| 4,349,921 A | 9/1982 | Kuntz |
| 4,369,769 A | 1/1983 | Edwards |
| 4,401,112 A | 8/1983 | Rezaian |
| 4,479,491 A | 10/1984 | Martin |
| 4,501,269 A | 2/1985 | Bagby |
| 4,553,273 A | 11/1985 | Wu |
| 4,554,914 A | 11/1985 | Kapp et al. |
| 4,599,084 A | 7/1986 | Nashef |
| 4,599,086 A | 7/1986 | Doty |
| 4,604,995 A | 8/1986 | Stephens et al. |
| 4,611,582 A | 9/1986 | Duff |
| 4,636,217 A | 1/1987 | Ogilvie et al. |
| 4,643,178 A | 2/1987 | Nastari et al. |
| 4,657,550 A | 4/1987 | Daher |
| 4,685,447 A | 8/1987 | Iversen et al. |
| 4,696,290 A | 9/1987 | Steffee |
| 4,714,469 A | 12/1987 | Kenna ................... 623/17 |
| 4,743,256 A | 5/1988 | Brantigan |
| 4,772,287 A | 9/1988 | Ray et al. |
| 4,790,303 A | 12/1988 | Steffee |
| 4,834,757 A | 5/1989 | Brantigan |
| 4,878,915 A | 11/1989 | Brantigan |
| 4,904,260 A | 2/1990 | Ray et al. |
| 4,904,261 A | 2/1990 | Dove et al. |
| 4,913,134 A | 4/1990 | Luque |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 5,011,484 A | 4/1991 | Breard |
| 5,015,247 A | 5/1991 | Michelson |
| 5,026,373 A | 6/1991 | Ray et al. |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,084,049 A | 1/1992 | Asher et al. |
| 5,092,866 A | 3/1992 | Breard et al. |
| 5,123,926 A | 6/1992 | Pisharodi |
| 5,167,662 A | 12/1992 | Hayes et al. |
| 5,180,381 A | 1/1993 | Aust et al. |
| 5,192,327 A | 3/1993 | Brantigan |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,352,225 A | 10/1994 | Yuan et al. |
| 5,387,213 A | 2/1995 | Breard et al. |
| 5,390,683 A | 2/1995 | Pisharodi |
| 5,395,372 A | 3/1995 | Holt et al. |
| 5,415,661 A | 5/1995 | Holmes |
| 5,443,514 A | 8/1995 | Steffee |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,514,180 A | 5/1996 | Heggeness et al. |
| 5,522,899 A | 6/1996 | Michelson ................... 623/17 |
| 5,534,028 A | 7/1996 | Bao et al. |
| 5,534,029 A | 7/1996 | Shima |
| 5,540,689 A | 7/1996 | Sanders et al. |
| 5,549,679 A | 8/1996 | Kuslich |
| 5,562,736 A | 10/1996 | Ray et al. |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi ................... 623/17 |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,766,252 A | 6/1998 | Henry et al. |
| 5,824,098 A | 10/1998 | Stein |
| 5,865,846 A | 2/1999 | Bryan et al. |
| 5,885,299 A | 3/1999 | Winslow et al. ............... 606/99 |
| 5,888,224 A | 3/1999 | Beckers et al. |
| 5,888,226 A | 3/1999 | Rogozinski ................... 623/17 |
| 5,976,186 A | 11/1999 | Bao et al. |
| 6,001,130 A | 12/1999 | Bryan et al. |
| 6,022,376 A | 2/2000 | Assell et al. |
| 6,113,639 A | 9/2000 | Ray et al. |
| 6,156,067 A | 12/2000 | Bryan et al. |
| 6,234,705 B1 | 5/2001 | Troxel |

FOREIGN PATENT DOCUMENTS

| | | |
|---|---|---|
| DE | 3113142 A1 | 1/1982 |
| EP | 140790 A2 | 10/1984 |
| EP | 146347 A1 | 12/1984 |
| EP | 322334 A1 | 12/1988 |
| EP | 0677277 A2 | 10/1995 |
| EP | 0767636 B1 | 4/1997 |
| EP | 1138268 | 4/2001 |
| FR | WO 90/00037 | 1/1990 |
| FR | 2681525 A1 | 3/1993 |
| FR | 2707864 A1 | 1/1995 |
| FR | 2717675 | 9/1995 |
| FR | 2722980 A1 | 2/1996 |
| FR | 2780269 A1 | 12/1999 |
| FR | 2782911 A1 | 3/2000 |
| FR | 2806614 | 9/2001 |
| FR | 2806616 | 9/2001 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

APPARATUS AND METHOD FOR DETERMINING IMPLANT SIZE

RELATED CASES

This application claims priority to United States Provisional Patent Application entitled APPARATUS AND METHOD FOR DETERMINING IMPLANT SIZE, filed Jul. 17, 2001, Serial No.: 60/306,099 and is a continuation-in-part of U.S. patent application Ser. No. 09/799,470 filed on Mar. 5, 2001 and entitled SPINAL IMPLANTS, INSERTION INSTRUMENTS, AND METHOD OF USE, which is a continuation-in-part of U.S. patent application Ser. No. 09/473,173 filed on Dec. 28, 1999 and entitled SPINE DISTRACTION IMPLANT, now U.S. Pat. No. 6,235,030 issued May 22, 2001, which is a continuation of U.S. patent application Ser. No. 09/179,570 filed on Oct. 27, 1998 and entitled SPINE DISTRACTION IMPLANT, now U.S. Pat. No. 6,048,342 issued Apr. 11, 2000, which is a continuation-in-part of U.S. patent application Ser. No. 09/175,645 filed on Oct. 20, 1998 and entitled SPINE DISTRACTION IMPLANT, now U.S. Pat. No. 6,068,630 issued May 30, 2000. All of the above applications and patents are incorporated herein by reference.

FIELD OF THE INVENTION

The present invention relates generally to a trial implant instrument. More particularly, the present invention relates to a trial implant instrument for determining the size of an implant location between adjacent spinous process.

BACKGROUND

As the present society ages, it is anticipated that there will be an increase in adverse spinal conditions which are characteristic of older people. By way of example, with aging comes increases in spinal stenosis (including but not limited to central canal and lateral stenosis), the thickening of the bones which make up the spinal column, and facet arthropathy. Spinal stenosis is characterized by a reduction in the available space for the passage of blood vessels and nerves. Pain associated with such stenosis can be relieved by medication and/or surgery. Of course, it is desirable to eliminate the need for major surgery for all individuals and in particular for the elderly.

Accordingly, there needs to be developed procedures and implants for alleviating such and other spine related condition, which are minimally invasive, which can be tolerated by the elderly and for that matter any individual, and which can be performed preferably on an outpatient basis.

Therefore, there is a need for a trial implant apparatus to determine the size of the location where the device will be implanted prior to performing the procedure. Such an apparatus and procedure will assist the physician to accurately select the correct size of the device to be implanted in the patient while minimizing the damage to tissue.

SUMMARY OF THE INVENTION

An object of the present invention is a trial implant device for determining the space between adjacent spinous process. Such a device has a sizer pivotally mounted with a handle so that the handle may rotate relative to the sizer.

Another object of the present invention is a method for determining the size between adjacent spinous process prior to implanting a device in the same area.

Other objects, aspects and features of the invention are evident from the description of the embodiments, the claims and the figures.

DETAILED DESCRIPTION OF THE INVENTION

Figure 1:
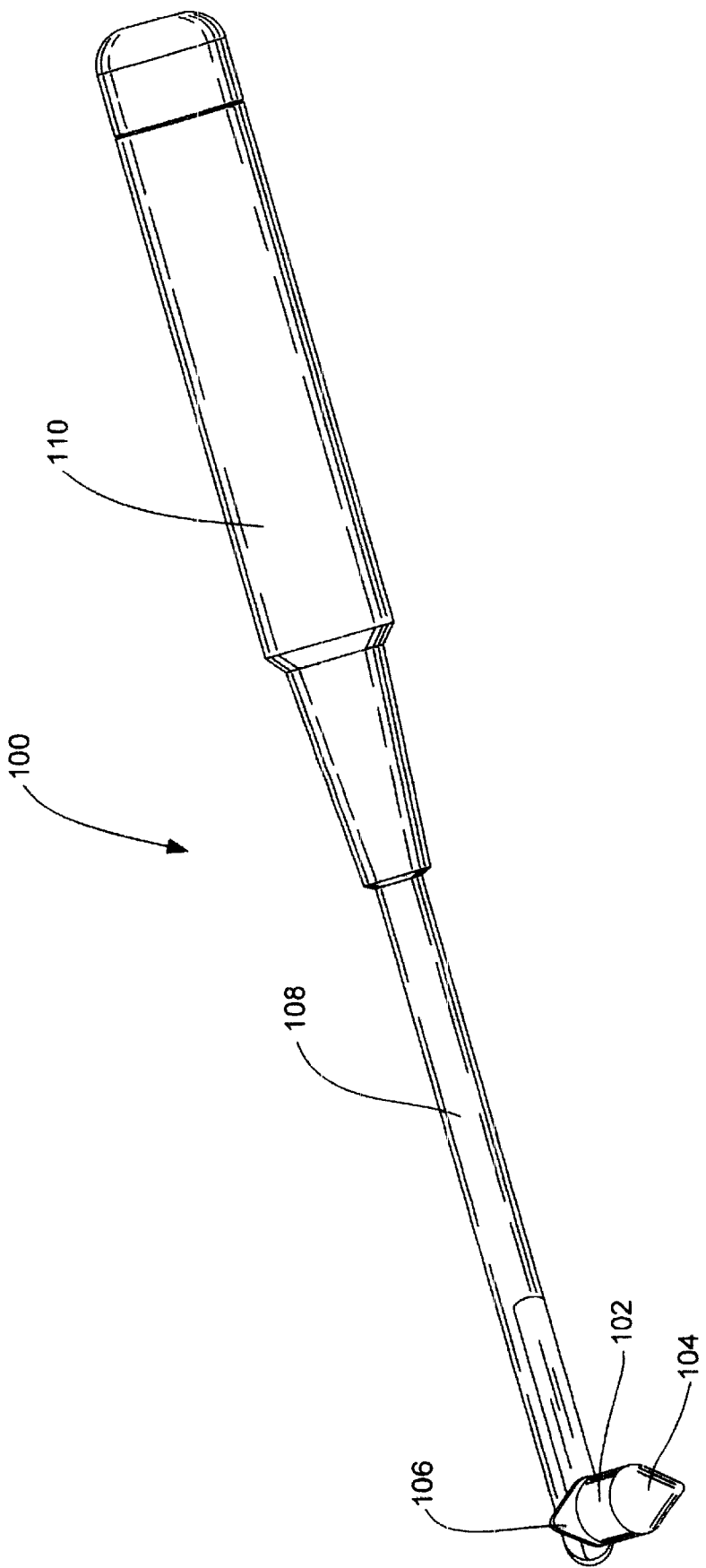
FIG. 1 is a perspective view of an embodiment of the present invention.
Figure 2:
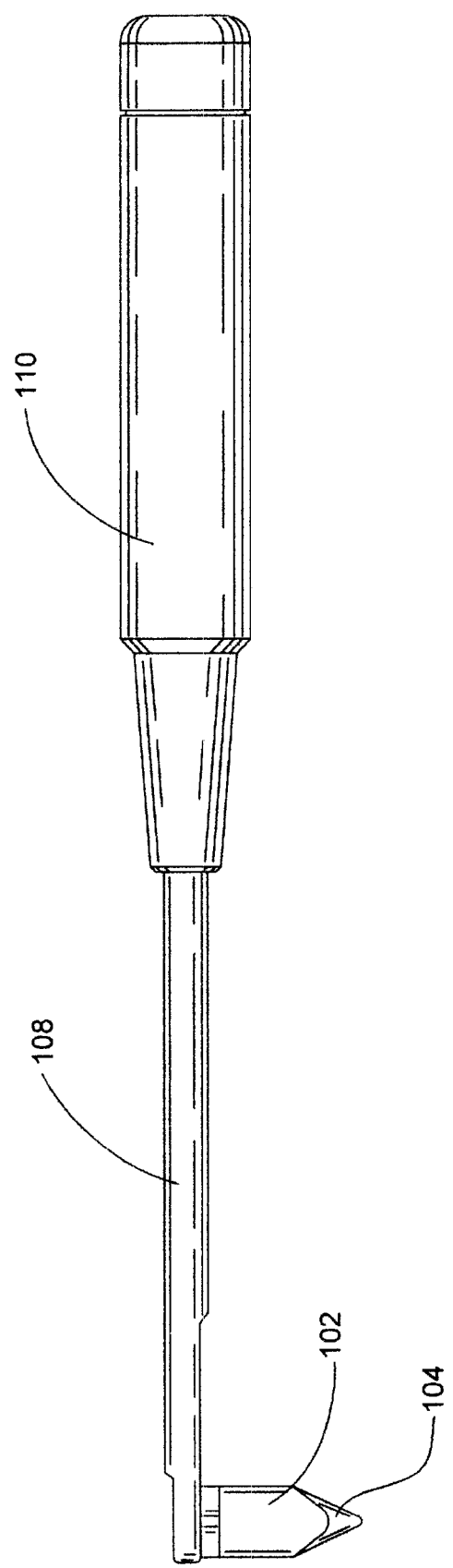
FIG. 2 is a side view of an embodiment of the present invention.
Figure 3:
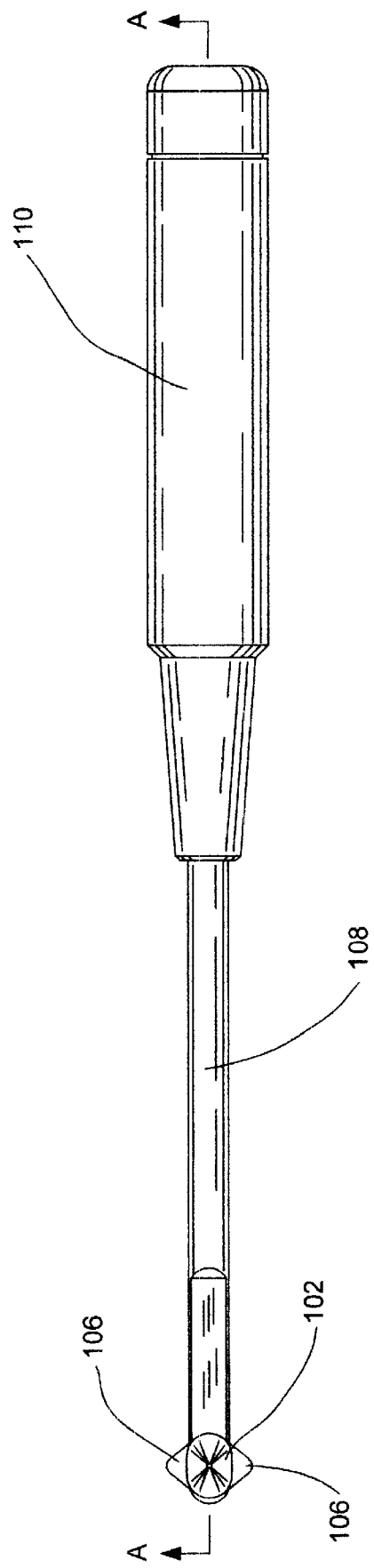
FIG. 3 is a front view of an embodiment of the present invention.

The trial implant instrument 100 is used for determining the space between adjacent spinous process. Referring now to FIGS. 1–3, the trial implant instrument 100 contains a sizer 102 and an elongated body 108.

Figure 4:
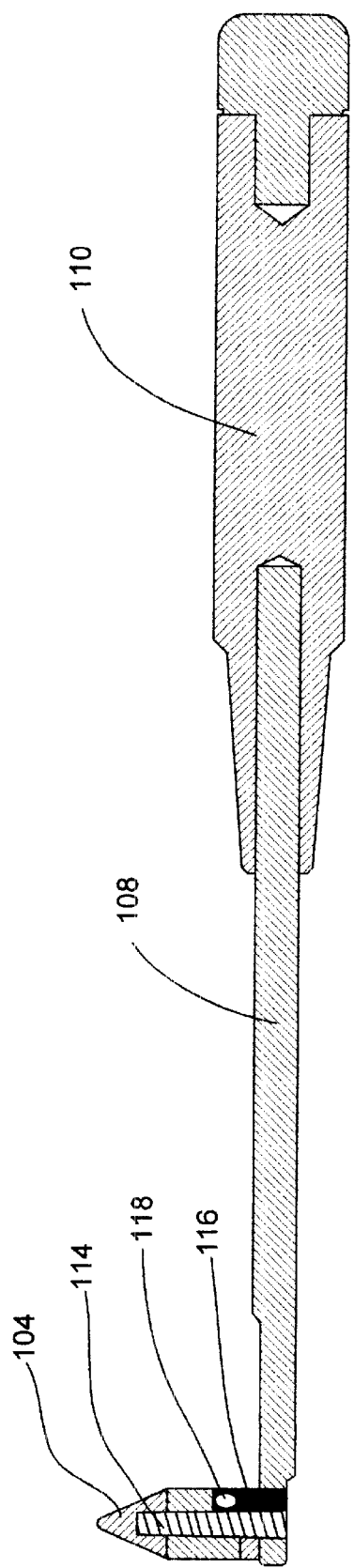
FIG. 4 is a cut-away view of an embodiment of the present invention from the perspective of line A—A in FIG. 3.
Figure 5:
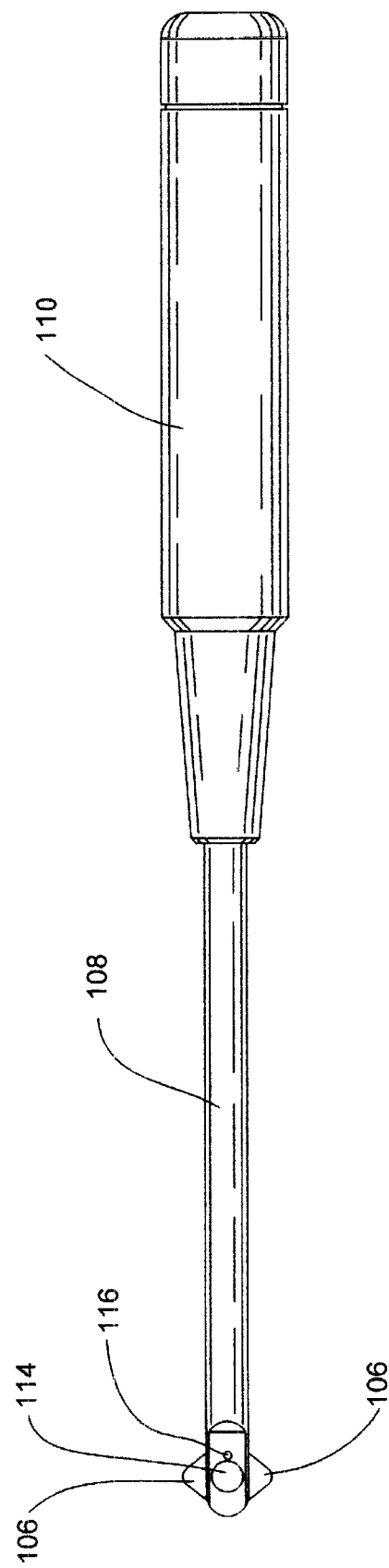
FIG. 5 is a rear view of an embodiment of the present invention.

The sizer 102 has a front end 104, flanges 106 and a track 118 (See FIG. 4). As illustrated by the embodiment of FIG. 3, the sizer 102 is generally cylindrical and substantially elliptical in cross-sectional shape. However, one of ordinary skill in the art will appreciate that the sizer 102 can comprise many different shapes and cross-sections, such as, but not limited to, circular, triangular, rectangular or egg-shaped.

The front end 104 preferably can penetrate the body tissue between adjacent spinous process so that the sizer 102 can be urged between adjacent spinous process. To accomplish this, the front end 104 must have a small diameter at the tip. The diameter of the front end 104 then gradually increases to the full diameter of the body of the sizer 102. Thus, once the front end 104 creates an opening, the front end 104 will distract the opening to the full diameter of the sizer 102. As shown in FIG. 2, the front end 104 is cone-shaped. Other shapes such as elliptical shapes, oval shapes, pyramid shapes and egg-shapes are also within the scope of the invention. By way of example only, the full smallest diameters of typical elliptical or oval sizers 102 are 6 mm, 8 mm, 10 mm, 12 mm, and 14 mm. In FIG. 3 the full smallest diameter is a long line drawn between the apexes of flanges 106.

As indicated above the sizer in FIG. 3 has two flanges 106. Both flanges 106 extend outward from the sizer 102. The flanges 106 prevent the sizer 102 from penetrating deeper than the length of the sizer 102. As illustrated by FIG. 3, the flanges 106 are triangular in shape with apexes and are located on opposite sides of the sizer 102. However, the flanges 106 can comprise other shapes such as, but not limited to, circular, rectangular or pyramid. The flanges 106 may also be a continuous strip of material extending out from the sizer 102, thus creating a rim around the sizer 102.

The track 118 is a curved cavity in the back surface of the sizer 102 (see FIG. 4). The track 118 preferably accepts a track pin 114 (described later) to limit the rotation of the sizer 104.

The handle 110 has a first cavity 111 for accepting the elongated body 108 and a second cavity 113 for accepting an insert 115 (FIG. 4). The handle 110 provides an area that a physician can grip to urge the sizer 102 between adjacent spinous process. The handle 110 is made of a convenient material, for example, Gray ULTEM™. Preferably, the insert 115 of the handle 110 has a color corresponding to the diameter of the sizer 102. By color coding each handle 110, a physician can differentiate between several trial implant instruments 100. For example, a gold insert 115 corresponds to a 6 mm diameter sizer 102. A green insert 115 corresponds to an 8 mm diameter sizer 102. A purple insert 115 corresponds to a 10 mm diameter sizer 102. A blue insert 115 corresponds to a 12 mm diameter sizer 102. Lastly, a gray insert 115 corresponds to a 14 mm diameter sizer 102. To further assist a physician to distinguish between several trial implant instruments 100, a diameter size can also be indicated on the bottom of the insert 115.

The elongated body 108 has a track pin 116 and a mounting pin 114. The sizer 102 is pivotally connected with the elongated body 108. The mounting pin 114 and the track pin 116 extend substantially perpendicular from the elongated body 108. The track pin 116 is parallel to the mounting pin 114. The mounting pin 114 engages the cavity 105 of the sizer 102 such that the sizer 102 rotates about the axis of the mounting pin 114. The mounting pin 114 can be threaded and the cavity can also be threaded in order to retain the sizer 102 on the mounting pin 114. Preferably, the range of rotation for the sizer 102 is restricted by the track pin 116 which engages the curved track 118. The range of rotation is limited because the track pin 116 extends into the curved track 118 and acts as a stopping mechanism when either end of the curved track 118 contacts the track pin 116. The range of rotation is limited to approximately a 60° range of motion in a preferred embodiment. However, the range of motion for the sizer 102 could be larger or smaller. In other embodiments the track 118 and track pin 116 can be eliminated if desired. Accordingly a physician is able to rotate the handle 110 through a specific range of motion while urging the sizer 102 between adjacent spinous processes, without placing any torsional forces on the sizer 102. Therefore, as the sizer 102 is being inserted between adjacent spinous process a physician can rotate the elongated body 108 and not cause additional damage to body tissue.

Spinal implant surgery can be carried out by using specially designed instruments to determine the correct size of an implant to be used. Several trial implant instruments 100 can be used successively to size the implant location in preparation for inserting the implant device in the patient.

A series of even larger instruments 100 can also be used to distract or separate apart the spinous process in order to ease the final implantation of the device that is left between the spinous process. After a surgical field is prepared, an incision or access port is made in the back of the patient. The intraspinous space is then accessed, and the trial implant instrument 100 can be used to determine the correct size of a spinal implant to be inserted into the patient between the spinous processes. Generally, the sizer 102 with the smallest diameter is inserted between the spinous processes first. If the sizer 102 is too loose in the interspinous process space, the sizer 102 is withdrawn from between the adjacent spinous process. The physician will then choose a trial implant instrument 100 with a larger diameter sizer 102. Then, the physician will urge the new sizer 102 between adjacent spinous process. This process continues until a sizer 102 encounters resistance indicating that the diameter of the sizer 102 is substantially equal to the size of the device to be implanted into the patient. A physician can then select an implant with the same diameter as the sizer 102, ensuring that the implant selected will properly fit between adjacent spinous process of the patient. Alternatively, the physician can select a larger diameter sizer to distract apart the spinous process an additional amount, if for example, there is a desire to place an implant with a larger diameter between the spinous process.

The diameter of the sizer 102 is intended to accurately represent the size of the implant device that will be inserted into the patient. Therefore, a physician should find the sizer 102 which, when inserted between adjacent spinous process, encounters resistance indicating that the proper sizer 102 has been selected. Specifically, inserting a sizer 102 of a known diameter between adjacent spinous process of a patient allows the physician to determine the correct size of the device that will be implanted between the adjacent spinous process prior to the actual procedure.

The foregoing description of preferred embodiments of the present invention has been provided for the purposes of illustration and description. It is not intended to be exhaustive or to limit the invention to the precise forms disclosed. Many modifications and variations will be apparent to practitioners skilled in the art. The embodiments were chosen and described in order to best explain the principles of the invention and its practical application, thereby enabling others skilled in the art to understand the invention with various embodiments and with various modifications as are suited to the particular use contemplated. It is intended that the scope of the invention be defined by the following claims and their equivalents.

What is claimed is:

1. A trial implant instrument for determining the space between adjacent spinous process, the instrument comprising:
   a sizer having a first end and a second end, whereas the first end forms a tip allowing the sizer to be easily inserted between adjacent spinous process, and the second end contains flanges extending therefrom to prevent the sizer from penetrating beyond a specific depth, and further contains a track to limit the rotation of the sizer;
   an elongated body having a first end and a second end, whereas the first end contains a handle portion so that a physician can urge the sizer between adjacent spinous process, and further whereas the second end contains a track pin and a mounting pin extending therefrom; and
   whereby the second end of the sizer is connected with the second end of the elongated body, so that once the sizer is inserted between adjacent spinous process, a physician may rotate the elongated body through a range of motion and not place any torsional forces upon the sizer.

2. The instrument according to claim 1, whereas the sizer is substantially elliptical in shape.

3. The instrument according to claim 1, whereas the sizer is substantially circular in shape.

4. The instrument according to claim 1, whereby the handle portion of the elongated body is color coded according to the diameter of the sizer.

5. The instrument according to claim 1, whereby the flanges are substantially triangular in shape and are located on opposite sides of the sizer.

6. The instrument according to claim 1, whereby the elongated body rotates about the axis of the mounting pin.

7. The instrument according to claim 6, whereby the elongated body can be rotated through approximately a 60° range of motion without placing a torsional force upon the sizer.

8. A trial implant instrument for determining the size between adjacent spinous process, the instrument comprising:
   a sizer having a first end, a second end, and a cavity extending through the second end, whereas the first end is cone shaped allowing the sizer to be easily inserted between adjacent spinous process, and the second end contains two flanges extending therefrom on opposite sides of the sizer to prevent the sizer from penetrating beyond a specific depth, and further contains a track to limit the rotation of the sizer;

an elongated body having a first end and a second end, whereas the first end contains a handle portion so that a physician can urge the sizer between adjacent spinous process, and further whereas the second end contains a track pin and a mounting pin extending therefrom; and whereby the second end of the sizer is connected with the second end of the elongated body so that once the sizer is inserted between adjacent spinous process, a physician may rotate the elongated body through a range of motion and not place any torsional forces upon the sizer.

9. The instrument according to claim 8, whereas the sizer is substantially circular in shape.

10. The instrument according to claim 8, whereas the sizer is substantially elliptical in shape.

11. The instrument according to claim 8, whereby the handle portion of the elongated body is color coded according to the diameter of the sizer.

12. The instrument according to claim 8, whereby the flanges are substantially triangular in shape and are located on opposite sides of the sizer.

13. The instrument according to claim 8, whereby the elongated body rotates about the axis of the mounting pin.

14. The instrument according to claim 13, whereby the elongated body may be rotated through approximately a 60° range of motion without placing a torsional force upon the sizer.

15. A method for determining the size of the implant location, the method comprising the steps of:
   (a) inserting a trial implant of a predetermined diameter between adjacent spinous process of a patient to a depth limited by a stop element, and if the trial implant encounters little resistance, withdrawing the trial implant;
   (b) inserting a trial implant of a larger diameter between adjacent spinous process of a patient to a depth limited by a stop element, and if the trial implant encounters little resistance, withdrawing the trial implant; and
   (c) repeating steps (a) and (b), whereby the diameter of each subsequent trial implant increases, until a trial implant encounters resistance indicating that the diameter of the trial implant is substantially equal to the diameter of a device to be implanted in the patient.

16. The method according to claim 15, whereby the method includes a plurality of trial implants, each with a different diameter.

17. The method according to claim 15, whereby the trial implant is connected with a handle device to assist the physician to insert the trial implant between adjacent spinous process, and further to assist the physician to remove the trial implant.

18. The method according to claim 15, whereby the stop element is a flange extending from the trial implant.

19. A trial implant instrument for determining the space between adjacent spinous process, the instrument comprising:

a sizer having a first end, a second end, and a cavity only extending through the second end, whereas the first end forms a tip allowing the sizer to be easily inserted between adjacent spinous process, and the second end contains flanges extending therefrom to prevent the sizer from penetrating beyond a specific depth, and further contains a track to limit the rotation of the sizer;

an elongated body having a first end and a second end, whereas the first end contains a handle portion so that a physician can urge the sizer between adjacent spinous process, and further whereas the second end contains a track pin extending therefrom to engage the track and a mounting pin extending therefrom to engage the cavity; and whereby the second end of the sizer is connected with the second end of the elongated body, so that once the sizer is inserted between adjacent spinous process, a physician may rotate the elongated body through a range of motion and not place any torsional forces upon the sizer.

20. The instrument according to claim 19, whereas the sizer is substantially elliptical in shape.

21. The instrument according to claim 19, whereas the sizer is substantially circular in shape.

22. The instrument according to claim 19, whereby the handle portion of the elongated body is color coded according to the diameter of the sizer.

23. The instrument according to claim 19, whereby the flanges are substantially triangular in shape and are located on opposite sides of the sizer.

24. The instrument according to claim 19, whereby the elongated body rotates about the axis of the mounting pin.

25. The instrument according to claim 24, whereby the elongated body can be rotated through approximately a 60° range of motion without placing a torsional force upon the sizer.

26. A trial implant for determining the space between adjacent spinous process, comprising:
   a trial sizer, adapted for insertion between adjacent spinous process;
   a handle; and
   whereby the trial sizer is movably connected with the handle.

27. The instrument according to claim 26, wherein the trial sizer is pivotably mounted to the handle.

28. The instrument according to claim 26, including a plurality of instruments, each with a trial sizer of a different size.

29. The instrument according to claim 26, including movement stops projecting from the handle that limit the movement of the sizer relative to the handle.

30. The instrument according to claim 26, including the sizer having a groove and the handle having a pin which extends into the groove, whereby the groove limits the movement of the handle relative to the trial sizer.

31. The instrument according to claim 26, whereas the trial sizer is substantially elliptical in shape.

32. The instrument according to claim 26, whereas the trial sizer is substantially circular in shape.

33. The instrument according to claim 26, whereby the handle is color coded according to the diameter of the sizer.

34. The instrument according to claim 26, whereby the trial sizer further has flanges that are substantially triangular in shape and are located on opposite sides of the sizer.

35. The instrument according to claim 26, whereby the handle further has a mounting pin extending therefrom by which the trial sizer rotates about the axis of the mounting pin.

36. The instrument according to claim 35, whereby once the trial sizer is inserted between adjacent spinous process, the handle can be rotated through approximately a 60° range of motion without placing a torsional force upon the trial sizer.

37. The apparatus of claim 26, wherein said trial sizer includes a strap flanges.

38. A trial implant instrument for determining the spacing between adjacent spinous process, comprising:
   a trial sizer, adapted for insertion between adjacent spinous process;
   a handle, adapted so that a physician can urge the trial sizer between adjacent spinous process; and
   means for movably connecting the trial sizer with the handle.

39. The instrument according to claim 38, wherein the trial sizer is pivotably mounted to the handle.

40. The instrument according to claim 39, whereby the handle is pivotally mounted to the trial sizer by a mounting pin extending from the handle, and further whereas the handle rotates about the axis of the mounting pin.

41. The instrument according to claim 40, whereby the handle can be rotated through approximately a 60° range of motion without placing a torsional force upon the trial sizer.

42. The instrument according to claim 38, including a movement stop projecting from the handle that limits the movement of the trial sizer relative to the handle.

43. The instrument according to claim 42, whereby the trial sizer has a groove and the handle has a pin which extends into the groove, with the groove limiting the movement of the pin and the handle relative to the trial sizer.

44. The instrument according to claim 38, whereas the trial sizer is substantially elliptical in shape.

45. The instrument according to claim 38, whereas the trial sizer is substantially circular in shape.

46. The instrument according to claim 38, whereby the handle is color coded according to the diameter of the trial sizer.

47. The instrument according to claim 38, whereby the trial sizer further includes flanges that are substantially triangular in shape and are located on opposite sides of the trial sizer.

48. A trial implant instrument for determining the spacing between adjacent spinous process, comprising:
   a trial sizer, adapted for insertion between adjacent spinous process;
   a handle, adapted so that a physician can urge the trial sizer between adjacent spinous process; and
   means for mounting the trial sizer with the handle in order to limit torsional force transfer between the handle and the trial sizer.

49. The instrument according to claim 48, wherein the trial sizer is pivotably mounted to the handle.

50. The instrument according to claim 49, whereby the trial sizer is pivotally mounted to the handle with a mounting pin that extends from the handle, and further whereas the handle rotates about the axis of the mounting pin.

51. The instrument according to claim 50, whereby the handle can be rotated through approximately a 60° range of motion without placing a torsional force upon the trial sizer.

52. The instrument according to claim 48, including a movement stop projecting from the handle that limits the movement of the trial sizer relative to the handle.

53. The instrument according to claim 48, including the trial sizer having a groove and the handle having a pin which extends into the groove, with the groove limiting the movement of the handle relative to the trial sizer.

54. The instrument according to claim 48, whereas the trial sizer is substantially elliptical in shape.

55. The instrument according to claim 48, whereas the trial sizer is substantially circular in shape.

56. The instrument according to claim 48, whereby the handle is color coded according to the diameter of the trial sizer.

57. The instrument according to claim 48, whereby the trial sizer further has flanges that are substantially triangular in shape and are located on opposite sides of the trial sizer.

58. A method for determining the size of the implant location, the method comprising the steps of:
   (a) inserting a trial sizer of a predetermined diameter, which is pivotally mounted to a handle, between adjacent spinous process of a patient, and if the trial sizer encounters little resistance, withdrawing the trial implant;
   (b) inserting a trial sizer of a larger diameter, which is pivotally mounted to a handle, between adjacent spinous process of a patient and if the trial sizer encounters little resistance, withdrawing the trial implant; and
   (c) repeating steps (a) and (b), whereby the diameter of each subsequent trial sizer increases, until a desired size is determined.

59. The method according to claim 58, whereby the method includes a plurality of trial sizers pivotally connected to a handle, each with a different diameter.

60. The method according to claim 58, whereby the trial sizer is pivotally connected to the handle to further allow a physician to rotate the handle through a range of motion and not place any torsional forces upon the trial sizer.

61. The method according to claim 60, whereby the handle can be rotated through approximately a 60° range of motion without placing a torsional force upon the trial sizer, resulting in less damage to the surround body tissue.

* * * * *